United States Patent
Guendel

(10) Patent No.: US 6,529,766 B1
(45) Date of Patent: Mar. 4, 2003

(54) METHOD FOR DISPLAYING THE TIP OF A MEDIAL INSTRUMENT SITUATED IN THE BODY OF A PATIENT

(75) Inventor: Lutz Guendel, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/447,896

(22) Filed: Nov. 23, 1999

(30) Foreign Application Priority Data

Nov. 27, 1998 (DE) .......................................... 198 54 905

(51) Int. Cl.⁷ ................................................. A61B 6/00
(52) U.S. Cl. ........................ 600/427; 600/411; 600/439
(58) Field of Search ................................. 600/427, 411, 600/439, 407; 606/130; 378/20, 21, 4

(56) References Cited

U.S. PATENT DOCUMENTS

| | | | | |
|---|---|---|---|---|
| 5,398,684 A | * | 3/1995 | Hardy | .......................... 600/425 |
| 5,627,868 A | * | 5/1997 | Nobuta et al. | ................. 378/19 |
| 5,841,830 A | * | 11/1998 | Barni et al. | ..................... 378/15 |
| 5,848,126 A | * | 12/1998 | Fujita et al. | ................. 378/195 |
| 6,031,888 A | * | 2/2000 | Ivan et al. | ..................... 378/20 |
| 6,101,234 A | * | 4/2000 | Ali et al. | ......................... 378/4 |
| 6,193,763 B1 | * | 2/2001 | Mackin | ...................... 624/427 |
| 6,203,497 B1 | * | 3/2001 | Dekel et al. | ................. 600/439 |
| 6,341,152 B1 | * | 1/2002 | Sugihara | .......................... 378/4 |

FOREIGN PATENT DOCUMENTS

EP    0 485 999    5/1992

* cited by examiner

*Primary Examiner*—Ruth S. Smith
(74) *Attorney, Agent, or Firm*—Schiff Hardin & Waite

(57) ABSTRACT

In a method for displaying the tip of a medical instrument situated in the body of the patient during a medical interventional procedure by means of an imaging method, data representing a number of planar slices of the patient are repeatedly acquired during the interventional procedure, and the data are subsequently analyzed to determine in which of the slices the tip of the instrument is situated. A signal that marks the slice is generated and a tomogram that corresponds to the slice marked by the signal is reconstructed and displayed.

34 Claims, 5 Drawing Sheets

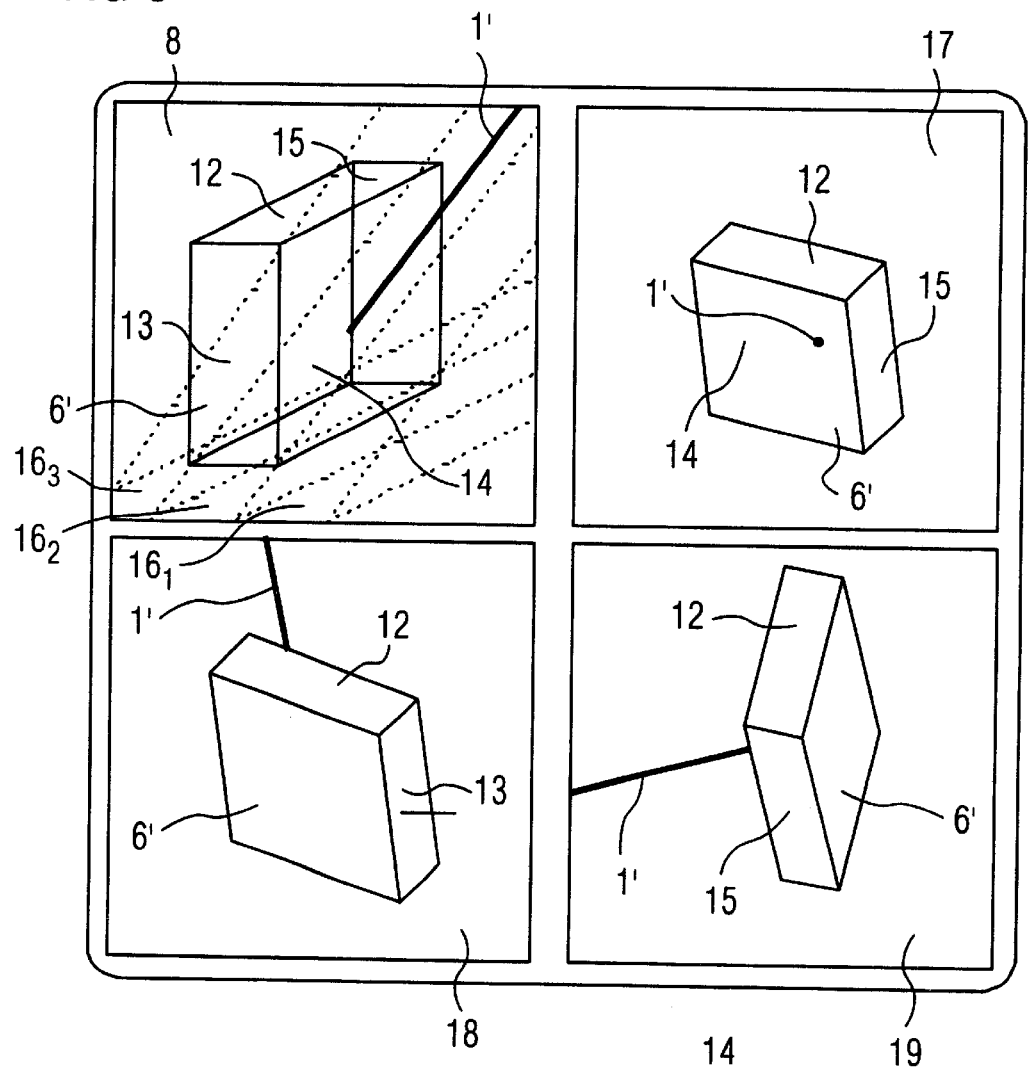

METHOD FOR DISPLAYING THE TIP OF A MEDIAL INSTRUMENT SITUATED IN THE BODY OF A PATIENT

BACKGROUND OF THE INVENTION

1. Field of the Invention

The present invention is directed to a method for displaying the tip of a medical instrument situated in the body of a patient during a medical interventional procedure by means of an imaging modality methods, 2. Description of the Prior Art Instruments, for example needles, laparoscopes etc., are introduced through the skin, through small orifices into the body of the patient during medical interventional procedures. The instruments are guided only according to "feel" or with the aid of an imaging diagnostic device, preferably with the aid of a tomography device or ultrasound.

In methods of the above type, the position of a slice of the body of the patient shown in a reconstructed image can be described, for example, by its position relative to the patient and its inclination relative to the longitudinal axis of the patient. As shown in FIG. 1, these parameters should be selected such that the instrument, for example a puncture needle 1 in a slice 2 of the body of the patient shown in a tomogram, can be guided to the desired object or site 3, for example to an organ of the patient. In the corresponding tomogram 4 shown in FIG. 2, it can be seen how the puncture needle 1, or actually its image 1' is guided to the object 3, or actually to its image 3'. In many cases, however, the instrument 1 cannot be moved as planned in the slice 2 shown in the tomogram, but exits this slice 2 and therefore can no longer be completely shown in the tomogram 4. as shown in the FIGS. 3 and 4.

The probability that the instrument will exit the slice shown in the tomogram can be reduced by the selection of a correspondingly thick slice that, when an X-ray CT device is used, can be realized by correspondingly adjusted diaphragms, by CvE tam superimposing neighbored slices, or by using a special reconstruction algorithm. The resolution of the tomogram, however, is reduced by such measures and the navigation of the instrument around sensitive body structures is made more difficult, or may be impossible. Alternatively, there is the possibility to reproduce a narrow slice and to manually correct the position of the slice shown in the tomogram when the instrument exits the slice, so that the instrument is visible again. This procedure, however, interrupts the work flow of the physician conducting the interventional procedure and is a source of prolongation of the duration of the interventional procedure, thus presenting a higher risk for the patient. This is also valid for other imaging methods.

European Application 0 485 999 discloses a method wherein a sectional plane can be marked in an X-ray shadow image (scanogram) by means of a cursor, with reference to which sectional plane a tomogram (tomographic image) is then reconstructed.

SUMMARY OF THE INVENTION

An object of the present invention is to provide a method of the type initially described wherein the danger of not being able to display the instrument by means of the imaging method is reduced, or precluded.

In a first inventive embodiment, this object is achieved in a method for displaying the tip of a medical instrument situated in the body of a patient during a medical interventional procedure by means of an imaging method, including the steps of repeatedly acquiring data for a number of planar slices of the patient during the interventional procedure, subsequently analyzing the data to identify in which of the slices the tip of the instrument is situated, and generating a signal that marks the slice that contains the tip of the instrument.

In this embodiment of the inventive method, because data representing a number of planar slices are acquired and since the slice in which the tip of the instrument is situated is identified, assuming that the planar slices cover a large enough region of the body of the patient, the danger that the instrument will exit the scanned region is minimal in practice. The acquisition of data for the planar slices and the reconstruction of enough images can ensue without problems so that an image resolution required for the particular interventional procedure is achieved.

In a preferred version of this embodiment, only that slice that is identified by the signal produced by the tip of the instrument is reconstructed by means of the imaging method and is displayed at a display unit. Therefore, the information that is initially required for carrying out the interventional procedure is available to the physician.

According to another version of this embodiment, data for the slice that is identified by the signal produced by the tip of the instrument are acquired by means of the imaging method so that the tip of the instrument is situated as a middle slice, among the number of acquired slices, at a start of the interventional procedure. This insures that, if the tip of the instrument deviates from the planned access path, leeway is present that is approximately of the same size in both directions. If an uneven number of slices is acquired, the middle slice is correspondingly oriented toward the planned access path of the instrument with respect to its position and its angle of inclination for this purpose. If an even number of slices is acquired, one of the two middle slices is correspondingly orientedand positioned.

If the tip of the instrument leaves the middle slice, the parameters of the data acquisition are adapted (modified), according to an embodiment, so that the tip of the instrument is currently again situated in a middle slice, i.e. the orientation and positioning of the acquired slices is automatically adapted to the path of the tip of the instrument.

Alternatively a visual indicator or an acoustic indicator can be generated via an output unit when the tip of the instrument leaves the original slice, i.e. when it leaves the currently displayed slice. In this case, the physician can then adapt the guidance of the instrument, or the parameters of the data acquisition, to current situation.

In a second embodiment of the invention, the aforementioned object is achieved in a method for displaying the tip of a medical instrument situated in the body of a patient during a medical interventional procedure by means of an imaging method, including the steps of repeatedly acquiring data from a volume of the body of the patient during the interventional procedure, three-dimensionally reconstructing the data and displaying the resulting three-dimensional data sets, at a display unit as three-dimensional data sets and/or as sections of three-dimensional data sets, i.e. as planar data sets. The three-dimensional data sets and/or the resulting planar data sets are analyzed with respect to the location of the tip of the instrument, whereupon a corresponding signal is generated.

Therefore, not only one tomogram of the planar slice in which the tip of the instrument is currently present is reconstructed, but a three-dimensional data set of the acquired volume of the body of the patient is generated. The conditions for various possibilities of displaying the region of the body of the patient containing the tip of the instrument are thus present.

According to a version of this second embodiment, a subject of the three-dimensional data set that contains the tip of the instrument is preferably displayed at the display unit as a three-dimensional data set and/or as sections of a three-dimensional data set, so that the image information required for carrying out the intervention, for example by selecting appropriate sectional planes from the three-dimensional data sets, is presented to the physician.

In a further version this second embodiment of the invention, a subset of the three-dimensional data set that contains the tip of the instrument is displayed as multi-planar slices, i.e. it is displayed by a number of parallel 2-dimensional slices, which are not necessarily parallel slices. The display of multi-planar slices is a precondition in order to achieve, under all circumstances according to a particularly preferred version of the invention, that the orientation of the displayed slice corresponds to the moving direction of the tip of the instrument. The directions defined by the multi-planar slices then can be used for the selection of the sections from the three-dimensional data set.

In the second embodiment, a visual indicator or an acoustic indicator can be generated via an output unit if the signal that marks the subset of the three-dimensional data set that contains the tip of the instrument originates from a different subset than the currently displayed subset of the three-dimensional data set.

Further, in the second embodiment a subset of the three-dimensional data set in which the tip of the instrument is currently present can be displayed if the tip of the instrument exits the formerly displayed subset of the three-dimensional data set.

In preferred versions of both embodiments of the invention, all data are acquired at the same time for the number of planar slices, or for a volume of the body during the interventional procedure, so that all planar slices, or the entire volume, represent only one point in time per repetition. Preferably, the data acquisition at the same time can ensue by means of an X-ray CT device having a two-dimensional arrangement of detector elements. Alternatively, the data can be acquired by means of a magnetic resonance (MR) device, an ultrasound device or by means of a different imaging modality.

DESCRIPTION OF THE DRAWINGS

FIG. 8 illustrates a further embodiment of the inventive method, wherein a volume is taken into consideration by data acquisition, reconstruction and evaluation, and the presentation ensues as a three-dimensional data set and as sections of the three-dimensional data set in the direction of the movement of the medical instrument and perpendicular thereto.

DESCRIPTION OF THE PREFERRED EMBODIMENTS

With an X-ray CT device with a two-dimensional arrangement of detector elements, for example a multiple line detector or an array detector, data for a number of substantially parallel slices of a body region of a patient, in which an organ to be punctured by means of a puncture needle is situated, are obtained at the same time. This preferably ensues in an operating mode of the X-ray CT device, in which operating mode the X-ray CT device employs a reduced X-ray dose compared to the preparation of conventional pickups.

The relative movement between the gantry and the patient bed is blocked during this data acquisition, if the X-ray CT device is a spiral CT device.

The X-ray CT device is operated such that the data acquisition, at the same time, of the number of parallel planar slices repeatedly ensues during the entire interventional procedure such that a number of tomograms of a least one slice are reconstructed and displayed pro second. This allows the physician to introduce the puncture needle into the body of the patient in a controlled manner by observation of the generated tomograms.

For carrying out an interventional procedure, the angle of tilt of the gantry of the X-ray CT device and the position of the bed of the X-ray CT device are initially adjusted such that the planned path of the tip of the puncture needle lies in a middle slice of the slices scanned by the X-ray CT device. In a known manner, the slice thicknesses of the scanned slices are adjusted corresponding to the desired resolution by a corresponding adjustment of diaphragms and/or the combination of data acquired by means of neighboring detector elements of the detector.

Figure 1:
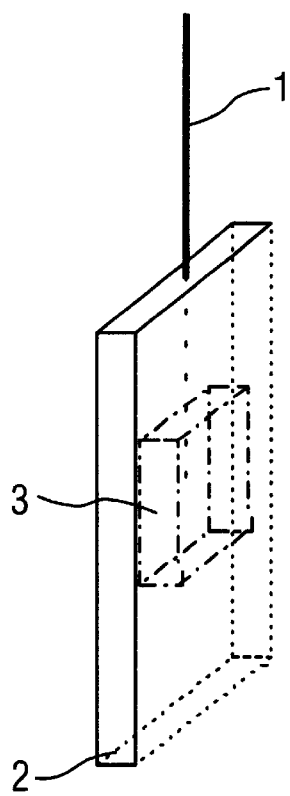
FIG. 1, as noted above, is a schematic, perspective view of an interventional procedure according to a conventional method.
Figure 2:
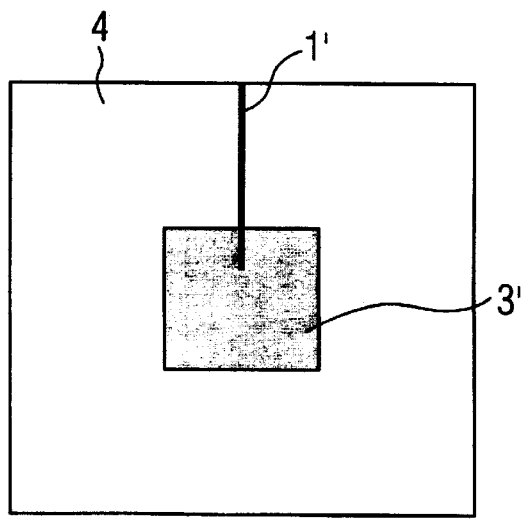
FIG. 2, as noted above, schematically illustrates a tomogram obtained in the method according to FIG. 1.
Figure 3:
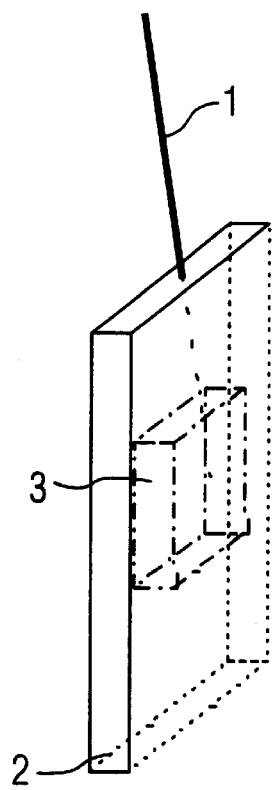
FIGS. 3 and 4, analogously to FIGS. 1 and 2, show the situation in the conventional method wherein the tip of the medical device exits the predetermined sectional plane.
Figure 4:
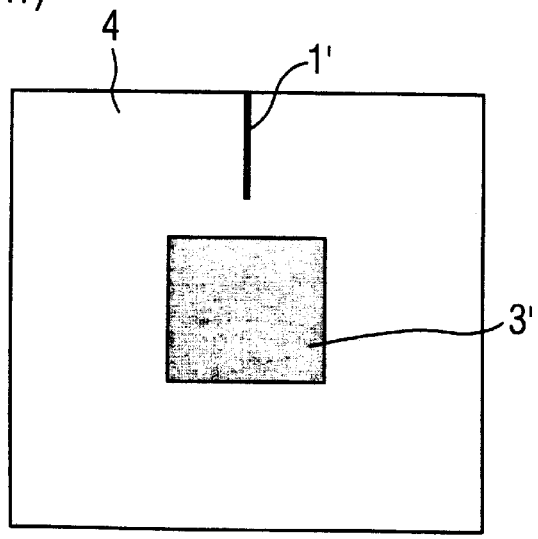
Figure 5:
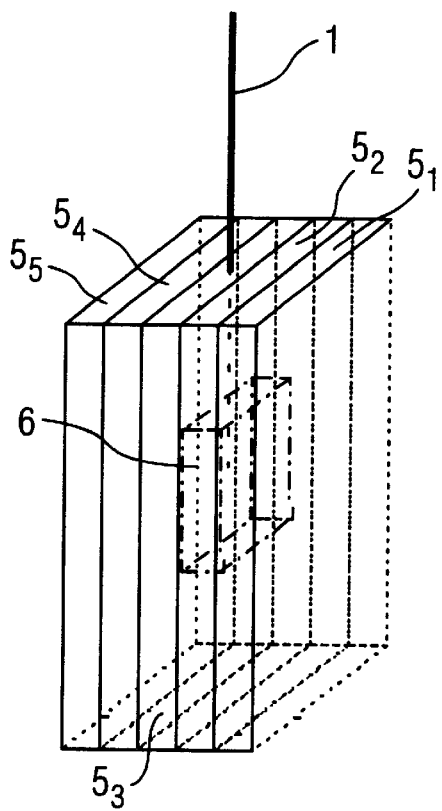
FIGS. 5 and 6, analogously to FIGS. 1 and 2, illustrate the inventive method, wherein a number of parallel slices are taken into consideration by data acquisition, reconstruction and evaluation.

Therefore, as shown in FIG. 5, data for a number of planar slices, for example five slices $5_1$ through $5_5$ are acquired, these slices being substantially parallel to one another and preferably adjacent to one another, as shown. The access path of the puncture needle 1 (shown in broken lines in FIG. 5) to an region (site) to be punctured lies in the middle slice $5_3$.

Figure 6:
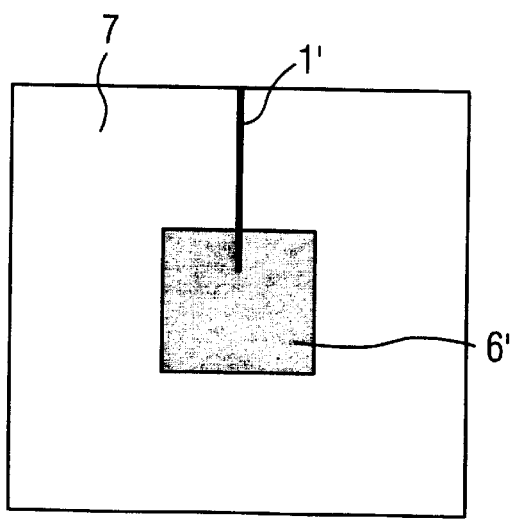

Tomograms of the slice $5_3$ are, with the aforementioned sequence frequency, acquired, reconstructed and displayed at a display unit. One of these tomograms, which is referenced 7, is shown in FIG. 6, wherein 1' is the image of the puncture needle and 6' is the image of the region to be punctured.

While the physician introduces the puncture needle 1 into the body of the patient, the X-ray CT device continuously analyzes the data corresponding to the slices $5_1$, $5_2$ and $5_4$, $5_5$ and/or the reconstructed images of these slices to determine in which of the slices $5_1$ through $5_5$ the tip of the puncture needle 1 is situated, and generates a signal that marks this slice. A tomogram of the corresponding slice, which should be the middle slice $5_3$ at the beginning of the interventional procedure, is reconstructed and displayed. When the signal marks a slice different from the currently displayed slice, this means the tip of the puncture needle 1 has exited the middle slice $5_3$ and is situated in one of the other slices $5_1$, $5_2$, $5_4$ or $5_5$; instead of the slice $5_3$. The currently-marked slice is reconstructed and the corresponding tomogram is displayed instead of the tomogram of the slice $5_3$. Therefore, the physician always can control the introduction of the puncture needle 1 on the basis of a tomogram of the slice in which the tip of the puncture needle 1 is currently situated.

In a different operating mode, the conditions of the data acquisition are modified, on the basis of the signal that marks the slice in which the tip of the puncture needle 1 is situated, so that the tip of the puncture needle 1 is situated again in the middle slice, which is reconstructed and displayed at the display unit. The adaption of the conditions of the data acquisition required for this purpose can ensue, for example, by adjusting the gantry and the patient bed, in an appropriate way, relative to one another or by using the output signals of other detector elements for the acquisition of data for the slices. The adaptation of the conditions of the data pickup can ensue fully-automatically or semi-automatically, whereby, in the latter case, it is indicated which adjustments of the X-ray CT device have to be undertaken by the physician in order to achieve that the tip of the puncture needle 1 is situated again in the middle slice $5_3$ of the picked up slices $5_1$ through $5_3$.

In a further operating mode, the signal that marks the slice in which the tip of the puncture needle 1 is situated causes the display of a corresponding visual indicator at the display unit of the X-ray CT device and/or the generation of an acoustic indicator if the tip of the puncture needle 1 exits the currently displayed slice $5_3$. By appropriate measures, whether by modified guidance of the puncture needle 1 or by modifying the conditions of the data acquisition, the physician can cause the tip of the puncture needle 1 to again be situated in the displayed slice so as to be visible in the displayed tomogram 7.

In another operating mode, the X-ray CT device follows the movement of the tip of the puncture needle 1 and estimates its further moving direction, which is then shown at the display unit, for example as a chromatically marked line, by the X-ray CT device. A corresponding indicator in visual or acoustic form ensues at the display unit if the estimated path proceeds through sensitive structures, which are characterized, for example, by preadjusted threshold values of the image information and/or by forms (template) that can be prescribed. Moreover, the computing processes that have to be undertaken by the X-ray CT device for the detection of the tip of the puncture needle are greatly accelerated by a limitation to the estimated path and its immediate environment.

Alternatively, the X-ray CT device can be operated such that data representing a volume of the body of the patient are repeatedly acquired during the interventional procedure, the data are three-dimensionally reconstructed and that the resulting three-dimensional data sets are displayed at the display unit as three-dimensional data sets and/or as sections of the three-dimensional data sets, i.e. as planar data sets. The data sets or sections can be displayed as a number of sub-images, for example four sub-images 8 through 11 (FIG. 7), or four sub-images 8 and 17 through 19 (FIG. 8), as in the case of the following exemplary embodiments.

Figure 7:
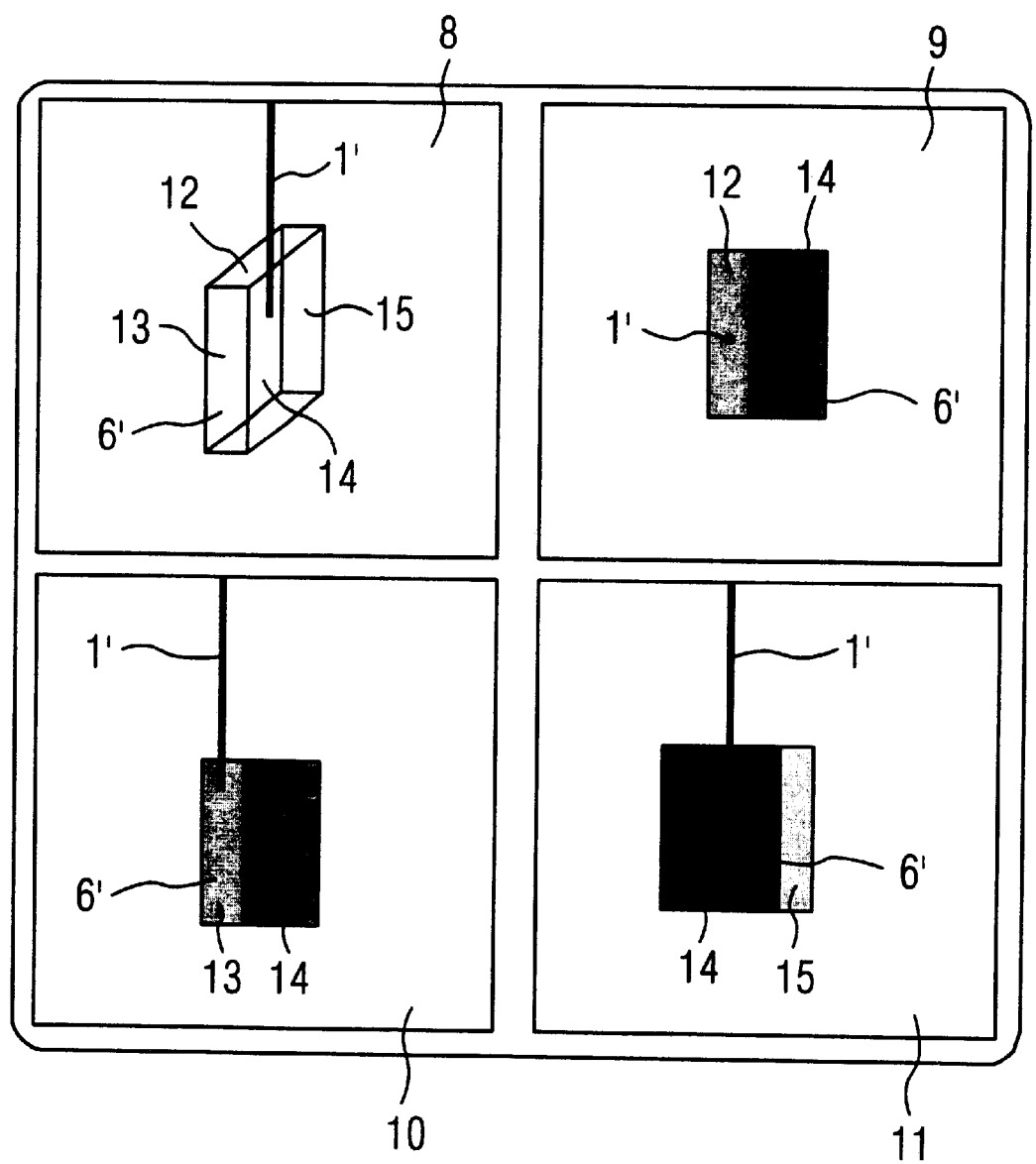
FIG. 7 shows the inventive method, wherein a volume is taken into consideration by data acquisition, reconstruction and evaluation, and the presentation ensues as a three-dimensional data set and as sections of the three-dimensional data set.

In a first operating mode as shown in FIG. 7, the sub-image 8, in which the image 1' of the puncture needle 1 and the image 6' of the region 6 to be punctured are shown in a perspective view, is marked for the presentation of the areas 12 through 15. The sub-image 9 represents a tomogram controlled by the position of the tip of the puncture needle 1 through the region 6 to be punctured at a viewing direction "from above". The areas 12 and 14 of the image 6' of the region 6 to be punctured thus can be seen. The sub-images 10 and 11 respectively represent the tomogram at a view "from front" with the areas 13 and 14 of the image 6' of the region 6 to be punctured, and "from the right side" with the areas 14 and 15 of the image 6' of the region 6 to be punctured.

In a further operating mode shown in FIG. 8, in the sub-image 8, in which the image 1' of the puncture needle 1 and the image 6' of the region 6 to be punctured are again shown in a perspective view, the areas 12 through 15 are marked for presentation. In the sub-image 8, a virtual slice $16_2$ is additionally defined within the three-dimensional data set along the moving direction of the puncture needle 1 and in this example—respective neighboring slices $16_1$, and $16_3$ are defined, which do not necessarily proceed parallel to the slices acquired by the X-ray CT device, and are therefore referred to as multi-planar slices. The sub-image 17 represents a tomogram controlled by the position of the tip of the puncture needle 1 through the three-dimensional object, seen in the moving direction of the puncture needle 1. The areas 12, 14 and 15 of the image 6' of the region 6 to be punctured thus can be seen. The sub-images 18 and 19, in the exemplary embodiment shown in FIG. 8, represent sections perpendicular to the moving direction of the puncture needle 1, wherein the areas 12 and 13, or the areas 12 and 15, of the image 6' of the region 6 to be punctured are respectively shown.

The inventive method has been explained above in an example wherein data acquisition ensues by means of an X-ray CT device. In the inventive method, however, the data acquisition can ensue using other devices, particularly a magnetic resonance (MR) device, an ultrasound device or with other imaging methods.

In the exemplary embodiment, the instrument to be introduced into the body of a patient is a puncture needle, however, the inventive method can also be executed in connection with other medical instruments.

The number of scanned slices and the geometry of the slices displayed in a tomogram in the case of the exemplary embodiment are only examples. Other numbers and other geometries are possible in the context of the invention.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for displaying a tip of a medical instrument situated in a body of a patient during a medical interventional procedure comprising the steps of:

during a medical interventional procedure which includes moving an instrument having a tip in a patient, conducting an imaging scan of said patient by repeatedly acquiring a single set of data representing and identifying a plurality of discrete planar slices of said patient;

automatically analyzing said data to determine in which slice of said plurality of planar slices said tip of said instrument is situated;

automatically generating a signal, from analyzing said data, which designates the slice in which the tip of the instrument is situated; and displaying an image of said patient reconstructed from said single set of data and containing a designation, dependent on said signal, of said slice in which said tip is situated.

2. A method as claimed in claim 1 comprising the additional step of reconstructing and displaying at a display unit a tomogram of said slice in which said tip of the instrument is situated and which is identified by said signal.

3. A method as claimed in claim 2 comprising monitoring movement of said tip of said instrument within said plurality of planar slices and, dependent on a progress of said movement of said tip, estimating a future path of movement of said tip of said instrument and displaying said future path on said display unit.

4. A method as claimed in claim 3 comprising including at least one of threshold values and predetermined forms in said plurality of planar slices displayed at said display unit and automatically generating an indicator signal if said estimated future path exceeds said threshold values or intersects said predetermined forms.

5. A method as claimed in claim 3 comprising analyzing only an immediate environment of said plurality of planar slices on said display unit surrounding said estimated future path to determine in which slice said tip of said instrument is situated.

6. A method as claimed in claim 1 comprising the step of acquiring, dependent on said signal, said data representing said plurality of planar slices so that said tip of said instrument is situated in a middle one of said plurality of planar slices on said display unit at a start of said interventional procedure.

7. A method as claimed in claim 6 comprising the steps of acquiring, under consideration of said signal, said data representing said plurality of planar slices, changing conditions for acquiring said data, dependent on said signal, to again cause said tip of said instrument to be situated in a middle one of said plurality of planar slices.

8. A method as claimed in claim 6 comprising automatically generating an indicator signal if said signal identifying said slice in which said tip of said instrument is situated identifies a slice in said plurality of planar slices which is different from said middle one of said plurality of planar slices.

9. A method as claimed in claim 1 comprising acquiring all of said data representing said plurality of planar slices of said patient at a same time in each repetition.

10. A method as claimed in claim 1 comprising acquiring said data using an X-ray computed tomography apparatus having a two-dimensional arrangement of radiation detector elements.

11. A method as claimed in claim 1 comprising acquiring said data using a magnetic resonance apparatus.

12. A method as claimed in claim 1 comprising acquiring said data using an ultrasound apparatus.

13. A method as claimed in claim 1 comprising acquiring said data using an X-ray exposure apparatus.

14. A method for displaying a tip of a medical instrument situated in a body of a patient during a medical interventional procedure comprising the steps of:

during a medical interventional procedure which includes moving an instrument having a tip in a patient, conducting a tomographic imaging scan of said patient by repeatedly acquiring a single set of data representing a volume of said patient;

reconstructing and identifying a plurality of tomograms of said volume;

converting said tomograms into a three-dimensional data set and automatically analyzing said three-dimensional data set to determine a location within said three-dimensional data set at which said tip of said instrument is situated;

automatically generating a signal, from analyzing said three-dimensional data set, which designates said location within said three-dimensional data set at which said tip of said instrument is situated; and displaying an image of said patient reconstructed from said single set of data and containing a designation, dependent on said signal, of said location at which said tip is situated.

15. A method as claimed in claim 14 comprising displaying, at a display unit a subset of said three-dimensional data set which contains said location.

16. A method as claimed in claim 15 comprising displaying said subset in which said location is contained as part of a tomogram at said display unit.

17. A method as claimed in claim 16 wherein said tomogram displayed at said display unit represent multi-planar slices of said patient.

18. A method as claimed in claim 17 wherein said multi-planar slices are not parallel.

19. A method as claimed in claim 17 wherein said instrument moves through said patient in a moving direction, and wherein said tip of said medical instrument is moved through said patient in said medical interventional procedure in a moving direction, and comprising orienting said multi-planar slices corresponding to said moving direction.

20. A method as claimed in claim 19 comprising automatically generating an indicator signal if said signal which identifies said location identifies a location outside of said subset displayed on said display unit as said tip proceeds in said moving direction.

21. A method as claimed in claim 15 comprising updating the subset on said display unit to always contain said location as said tip proceeds in said moving direction.

22. A method as claimed in claim 14 displaying a plurality of sectional planes, in said three-dimensional data set on said display unit.

23. A method as claimed in claim 22 comprising using a current location of said tip of said instrument to define a position of said sectional planes.

24. A method as claimed in claim 15 comprising monitoring movement of said tip of said instrument within said three-dimensional data set and, dependent on a progress of said movement of said tip, estimating a future path of movement of said tip of said instrument and displaying said future path on said display unit.

25. A method as claimed in claim 24 comprising including at least one of threshold values and predetermined forms in said three-dimensional data set displayed at said display unit, and automatically generating an indicator signal if said estimated future path exceeds said threshold values or intersects said predetermined forms.

26. A method as claimed in claim 24 comprising displaying only a portion of said three-dimensional data set at said display unit which surrounds said future path of movement of said tip.

27. A method as claimed in claim 24 comprising displaying a plurality of sectional planes from said three-dimensional data set which are not necessarily parallel to each other in which said future path of movement of said tip proceeds.

28. A method as claimed in claim 27 comprising utilizing said estimated future path and a portion of said three-dimensional data set surrounding said future path for identifying which of said sectional planes said tip of said instrument is situated on said display unit.

29. A method as claimed in claim 15 comprising automatically generating an indicator signal if said signal identifying said location at which said tip of said instrument is situated identifies a subset of said three-dimensional data set which is different from said subset displayed at said display unit.

30. A method as claimed in claim 14 comprising acquiring all of said data representing said plurality of tomograms said patient at a same time in each repetition.

31. A method as claimed in claim 14 comprising acquiring said data using an X-ray computed tomography apparatus having a two-dimensional arrangement of radiation detector elements.

32. A method as claimed in claim 14 comprising acquiring said data using a magnetic resonance apparatus.

33. A method as claimed in claim 14 comprising acquiring said data using an ultrasound apparatus.

34. A method as claimed in claim 14 comprising acquiring said data using an X-ray exposure apparatus.

\* \* \* \* \*